(12) United States Patent
Nordang (10) Patent No.: US 8,133,339 B2
(45) Date of Patent: Mar. 13, 2012

(54) BONDING OF ELASTOMERIC SUBSTRATE UNDER STRETCHED CONDITIONS

(75) Inventor: Lars N. Nordang, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 207 days.

(21) Appl. No.: 12/707,169

(22) Filed: Feb. 17, 2010

(65) Prior Publication Data

US 2010/0139846 A1    Jun. 10, 2010

Related U.S. Application Data

(63) Continuation of application No. 11/303,074, filed on Dec. 14, 2005, now abandoned.

(51) Int. Cl.
*B32B 37/00* (2006.01)
(52) U.S. Cl. ......... 156/164; 156/160; 156/163; 156/229
(58) Field of Classification Search ................... 156/160, 156/163, 164, 229
See application file for complete search history.

(56) References Cited

U.S. PATENT DOCUMENTS

| | | | |
|---|---|---|---|
| 3,692,618 A | 9/1972 | Dorschner et al. |
| 3,849,241 A | 11/1974 | Butin et al. |
| 4,340,563 A | 7/1982 | Appel et al. |
| 4,655,760 A | 4/1987 | Morman et al. |
| 4,657,802 A | 4/1987 | Morman |
| 4,720,415 A | 1/1988 | Wielen et al. |
| 4,741,949 A | 5/1988 | Morman et al. |
| 4,781,966 A | 11/1988 | Taylor |
| 4,789,699 A | 12/1988 | Kieffer et al. |
| 4,803,117 A | 2/1989 | Daponte |
| 4,854,984 A | 8/1989 | Ball et al. |
| 4,919,738 A | 4/1990 | Ball et al. |
| 4,965,122 A | 10/1990 | Morman |
| 4,981,747 A | 1/1991 | Morman |
| 5,114,781 A | 5/1992 | Morman |
| 5,116,662 A | 5/1992 | Morman |

(Continued)

FOREIGN PATENT DOCUMENTS

EP    0432755    6/1991

(Continued)

OTHER PUBLICATIONS

International Search Report PCT/US2006/032206 mailed Feb. 2, 2007.

*Primary Examiner* — Jeff Aftergut
(74) *Attorney, Agent, or Firm* — Dority & Manning, P.A.

(57) ABSTRACT

A method of bonding material in a process system for producing a bonded product includes the steps of loading a plurality of rolls of elastomeric material in an unwind system; programming a controller with an unwind speed and a rewind speed, the controller in communication with the unwind system and a rewinder disposed downstream from the unwind system for respective communication of the unwind and rewind speeds to the unwind system and the rewinder; unwinding a quantity of material from the plurality of rolls of elastomeric material into a pressure bonder disposed upstream of the rewinder, the pressure bonder and the rewinder operating faster than the unwind system operating at the unwind speed to generate a speed differential, wherein the speed differential imparts a stretch state to the quantity of material; and bonding the stretched quantity of material with the pressure bonder.

23 Claims, 4 Drawing Sheets

U.S. PATENT DOCUMENTS

| | | |
|---|---|---|
| 5,226,992 A | 7/1993 | Morman |
| 5,336,545 A | 8/1994 | Morman |
| 5,609,702 A | 3/1997 | Andersen |
| 5,647,864 A | 7/1997 | Allen et al. |
| 5,763,041 A | 6/1998 | Leak et al. |
| 6,114,263 A | 9/2000 | Benson |
| 6,340,782 B1 * | 1/2002 | Kling et al. .................. 604/366 |
| 6,627,564 B1 | 9/2003 | Morman |
| 6,740,200 B2 | 5/2004 | Seymour et al. |
| 6,969,441 B2 | 11/2005 | Welch et al. |
| 7,108,759 B2 | 9/2006 | You et al. |
| 2002/0153086 A1 | 10/2002 | Alper |
| 2004/0006323 A1 | 1/2004 | Hall |
| 2004/0102754 A1 | 5/2004 | Morman et al. |
| 2006/0148358 A1 * | 7/2006 | Hall et al. ..................... 442/328 |
| 2006/0258249 A1 | 11/2006 | Fairbanks |
| 2006/0266473 A1 | 11/2006 | Senapati et al. |

FOREIGN PATENT DOCUMENTS

EP 0432763 6/1991

* cited by examiner

BONDING OF ELASTOMERIC SUBSTRATE UNDER STRETCHED CONDITIONS

RELATED APPLICATIONS

The present application is a continuation application and claims priority to U.S. patent application Ser. No. 11/303,074 filed on Dec. 14, 2005, now abandoned. The disclosure of which is hereby incorporated by reference.

BACKGROUND OF THE INVENTION

Disposable garments, such as infant and children's diapers, swimwear and training pants, as well as adult incontinence garments, conventionally include materials that are joined together and connected using a bonding process, or the materials are bonded in related converting systems prior to bonding the materials together. For example, a training pant or other pant-type garment may have a front side panel and a back side panel that are bonded together at a side seam to provide a complete side panel. The side panels are typically connected at the side seam using an ultrasonic process such as the process described by You et al. in U.S. Pat. App. Pub. No. 2005/0133144 A1.

The ability to form strong ultrasonic bonds using conventional processes is limited by several factors, including the process converting speeds or production line speeds, bonding time or dwell time, and the thickness and/or basis weight of the materials being bonded. Moreover, in the case of rotary ultrasonic or pressure bonding of high loft substrates, bonding pattern roll pins have a tendency of piercing the elastomeric material instead of creating a suitable bond.

A bonding process that provides sufficient bond strength for high loft substrates and does not decrease production line speeds is needed in the industry.

SUMMARY OF THE INVENTION

The present invention is generally directed to a method of bonding high loft substrates efficiently by placing the high loft substrate in a stretched condition in preparation for bonding. According to an aspect of the invention, this can be readily achieved by feeding in less substrate to the process than an amount of substrate being extracted from the process. Generally, a lower loft substrate results, which is more suitable for bonding. The component parts of the bonding system are simple, reliable and economical to manufacture and use. Other advantages of the invention will be apparent from the following description and the attached drawings or can be learned through practice of the invention.

In one aspect of the invention, a method of bonding material in a process system for producing a bonded product includes the steps of loading a plurality of rolls of elastomeric material in an unwind system; programming a controller with an unwind speed and a rewind speed, the controller in communication with the unwind system and a rewinder disposed downstream from the unwind system for respective communication of the unwind and rewind speeds to the unwind system and the rewinder; unwinding a quantity of material from the plurality of rolls of elastomeric material into a pressure bonder system disposed upstream of the rewinder, the pressure bonder system and the rewinder operating faster than the unwind system operating at the unwind speed to generate a speed differential, wherein the speed differential imparts a stretched state to the quantity of material; and bonding the stretched quantity of material with a pressure bonder of the pressure bonder system. The plurality of rolls of elastomeric material can include a high loft elastomeric material. The plurality of rolls of elastomeric material can also include a stretch bonded laminate, a vertical filament stretch bonded laminate, a continuous filament stretch bonded laminate or combinations of these laminates. Further, the quantity of material can be polyesters, polyolefins and combinations thereof.

Also in this aspect of the invention, the unwind system can have an unwinder for unwinding at least one of the rolls of elastomeric material. Further in this aspect, the controller can be a computer or a programmable logic controller to program the rewind speed at least twice as fast as the unwind speed. In one example, the unwind speed is from about 600 feet per minute to about 1200 feet per minute, although the unwind speed can be orders of magnitude slower or faster with the rewind speed being at least somewhat faster than the unwind speed.

Further in this aspect of the invention, the pressure bonder can have a pattern roll and an anvil for exerting a pressure to bond the quantity of material with a pattern between the pattern roll and the anvil. For example, the pressure can be a lineal pressure of about $0.05*10^6$ N/m up to about $6*10^6$ N/m.

Alternatively, or additionally, the pressure bonder in this aspect of the invention can include a bonding roll and an anvil, which exert a pressure such as the pressure noted above to induce internal heating in the quantity of material to fuse a plurality of fibers of the quantity of material into a bond between the pattern roll and the anvil.

Still further in this aspect of the invention, the method of bonding material can include at least two rolls providing respective first and second quantities of material. The first and second quantities of material can be stretched equally before bonding by the pressure bonder. Also, one or more of the quantities of material can stretched from about 25% to about 200% before bonding by the pressure bonder, more particularly, from about 50% to about 150% before bonding by the pressure bonder. The quantities of material can be stretched in a machine direction or transverse to the machine direction before bonding by the pressure bonder, or the quantities of material can be stretched transverse to the machine direction and in the machine direction before bonding by the pressure bonder. In these aspects of the invention, the bonding step imparts a bond to the quantity of material having a bond strength greater than a material strength of the quantity of material such that material failure of the quantity of material occurs before failure of the bond.

Also in this aspect of the invention, the plurality of rolls of elastomeric material can be a single roll and the quantity of material can be folded at least once to generate at least two layers of material, the at least two layers of material being equally stretched before bonding by the pressure bonder.

Further in this aspect of the invention, the quantity of material can be nipped with a nip to stretch the quantity of material before bonding by the pressure bonder, the nip being disposed between the unwind system and the rewinder and operating at the unwind speed.

In another aspect of the invention, a method of bonding material in a process system for producing a bonded product includes the steps of loading a first roll of high loft elastomeric material in a first unwinder and a second roll of high loft elastomeric material in a second unwinder; programming a controller with an unwind speed and a rewind speed, the controller in communication with the first and second unwinders and a rewinder disposed downstream from the first and second unwinders for respective communication of the unwind and rewind speeds to the first and second unwinders and the rewinder; unwinding a first quantity of material from the first roll and a second quantity of material from the second roll into a nip disposed upstream of a pressure bonder system, the pressure bonder system and the rewinder operating faster than the first and second unwinders and the nip to generate a speed differential, wherein the speed differential imparts a stretched state to the first and second quantities of material; and bonding the stretched first and second quantities of material together with a pressure bonder of the pressure bonder system. In this aspect, the first and second quantities of material can be a high loft elastomeric material, a stretch bonded laminate, a vertical filament stretch bonded laminate, a continuous filament stretch bonded laminate, a polyester, a polyolefin and combinations of these.

Also in this aspect of the invention, the controller can be a computer or a programmable logic controller to control the rewind speed at least twice as fast as the unwind speed.

Further in this aspect, the pressure bonder includes a pattern roll and an anvil, the pattern roll and the anvil being configured to exert a pressure to bond the first and second quantities of material with a pattern between the pattern roll and the anvil. Alternatively or additionally, the pressure bonder includes a bonding roll and an anvil, the bonding roll and the anvil being configured to exert a pressure to induce internal heating in the first and second quantities of material to fuse a plurality of fibers of the first and second quantities of material into a bond between the pattern roll and the anvil. The quantities of material are stretched from about 25% to about 200% before bonding by the pressure bonder, more particularly, from about 50% to about 150% before bonding by the pressure bonder. The quantities of material can be stretched in a machine direction before bonding by the pressure bonder, or the quantities of material can be stretched transverse to a machine direction before bonding by the pressure bonder. Alternatively, the quantities of material can be stretched transverse to the machine direction and in the machine direction before bonding by the pressure bonder. In this aspect, the bonding step imparts a bond to the quantities of material having a bond strength greater than a material strength of the quantities of material such that material failure of the quantities of material occurs before failure of the bond. Also in this aspect, at least one of the quantities of material can be folded at least once to generate at least two layers, the at least two layers being equally stretched before bonding by the pressure bonder.

In yet another aspect of the invention, a method of bonding material in a process system for producing a bonded product includes the steps of providing a roll of elastomeric material; programming a controller with a first speed and a second speed, the controller in communication with the roll of elastomeric material and a bonder system disposed downstream from the roll of elastomeric material for respective communication of the first and second speeds to the roll of elastomeric material and the bonder system; feeding a quantity of material from the roll of elastomeric material at the first speed into the bonder system, the bonder system operating at the second speed faster than the first speed to generate a speed differential, wherein the speed differential imparts a stretched state to the quantity of material; and bonding the stretched quantity of material with a bonder of the bonder system. In this aspect, the roll of elastomeric material is a high loft elastomeric material. Also in this aspect of the invention, the controller can be a computer or a programmable logic controller for controlling the first and second speeds; for example, to set the first speed at least twice as fast as the second speed Other features and aspects of the invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeat use of reference characters in the present specification and drawings is intended to represent the same or analogous features or elements of the present invention.

DEFINITIONS

Within the context of the present description, the following terms may have the following meanings:

"Machine direction" (MD) refers to the length of a fabric or material in the direction in which it is produced or converted, as opposed to "cross direction" or "cross-machine direction" (CD or CMD), which refers to the width of a fabric in a direction generally perpendicular to the machine direction.

"Attached" and "joined" refers to the bonding, adhering, connecting, and any other method for attaching or joining two elements. Two elements will be considered to be attached or joined together when they are bonded directly to one another or indirectly to one another, such as when each is directly attached to an intermediate element.

"Sheet" refers to a layer, which may be a film, a foram, or a nonwoven web.

"Member" when used in the singular can refer to a single element or a plurality of elements.

The term "composite nonwoven fabric", "composite nonwoven", "laminate", or "nonwoven laminate", as used herein, unless otherwise defined, refers to a material having at least one elastic material joined to at least one sheet material. In most embodiments such laminates or composite fabric will have a gatherable layer, which is bonded to an elastic layer or material so that the gatherable layer may be gathered between bonding locations. As set forth herein, the composite elastic laminate may be stretched to the extent that the gatherable material gathered between the bond locations allows the elastic material to elongate. This type of composite elastic laminate is disclosed, for example, in U.S. Pat. No. 4,720,415 to Vander Wielen et al., which is incorporated herein in its entirety by reference thereto.

As used herein, the term "nonwoven web" refers to a web having a structure of individual fibers or threads that are interlaid, but not in an identifiable, repeating manner. Nonwoven webs have been, in the past, formed by a variety of processes such as, for example, meltblowing processes, spunbonding processes and bonded carded web processes.

The term "continuous filaments", as used herein, refers to strands of continuously formed polymeric filaments. Such filaments will typically be formed by extruding molten material through a die head having a certain type and arrangement of capillary holes therein.

As used herein, the term "meltblown fibers" means fibers formed by extruding a molten thermoplastic material through a plurality of fine, usually circular, die capillaries as molten thermoplastic material or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, U.S. Pat. No. 3,849,241 to Butin, which is incorporated herein in its entirety by reference thereto.

As used herein, the term "spunbonded fibers" refers to small diameter fibers formed by extruding a molten thermoplastic material as filaments from a plurality of fine, usually circular, capillaries of a spinerette with the diameter of the extruded filaments then being rapidly reduced as by, for example, eductive stretching or other well-known spun-bonding mechanisms. The production of spun-bonded nonwoven webs is illustrated in patents such as, for example, U.S. Pat. Nos. 4,340,563 to Appel et al., and 3,692,618 to Dorschner et al. The disclosures of these patents are incorporated herein in their entireties by reference thereto.

"Extendable" or "extensible" means that property of a material or composite by virtue of which it stretches or extends in the direction of an applied biasing force by at least about 25% of its relaxed length. An extendable material does not necessarily have recovery properties. For example, an elastomeric material is an extendable material having recovery properties. A meltblown web may be extendable, but not have recovery properties and, thus, be an extensible but non-elastic material.

"Elastomeric," "elastic," and "elasticized" refer to a material or composite which can be stretched or elongated by at least 25% of its relaxed length and which will recover, upon release of the applied force, at least 10% of its elongation. It is generally preferred that the elastomeric material or composite be capable of being elongated by at least 100%, more preferably by at least 300%, of its relaxed length and recover at least 50% of its elongation.

"Non-extensible" refers to a material that does not stretch or extend by at least about 25% of its relaxed length without fracture upon application of a biasing force. Materials that are extensible or elastomeric are not considered "non-extensible."

"Untensioned" as used herein to describe a material web does not mean lacking all tension. In order to handle and process moving webs, some moderate amount of tension is needed to hold the web or material in place. An "untensioned" web or material, as used herein, is under enough tension to process the material, but less than that required to cause substantial deformation of the material.

"Necked material" refers to any material, which has been constricted in at least one dimension by processes such as, for example, drawing.

"Neck-bonded" laminate refers to a composite material having an elastic member that is bonded to a member while the member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Reversibly-necked material" refers to a necked material that has been treated while necked to impart memory to the material so that when force is applied to extend the material to it pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is described in U.S. Pat. Nos. 4,965,122 and 4,981,747, incorporated herein by reference for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,789,699, 4,781, 966, 4,720,415, 4,657,802, and 4,655,760, which are incorporated herein by reference in their entirety for all purposes.

"Neck stretch-bonded" laminate refers a laminate made from the combination of a neck-bonded laminate and a stretch-bonded laminate. Examples of necked stretch bonded laminates are disclosed in U.S. Pat. Nos. 5,114,781 and 5,116, 662, which are incorporated herein in their entirety by reference thereto for all purposes. A necked stretch bonded laminate can be stretchable in both the machine and cross-machine directions.

Various aspects and embodiments of the invention will be described in the context of a material for disposable absorbent articles, such as disposable diapers, children's training pants, incontinence articles, feminine care products, diaper pants, disposable swim pants and the like. It should be appreciated that this is for illustrative purposes only, and that the invention is not limited to any particular absorbent article or absorbent articles in general. The material according to the invention may have beneficial uses in any number of applications, such as protective medical clothing, drapes, gowns and the like.

It is to be understood by one of ordinary skill in the art that the present discussion is a description of exemplary embodiments only, and is not intended as limiting the broader aspects of the present invention.

DETAILED DESCRIPTION

The present disclosure is generally directed to a method for producing a bonded substrate. More particularly, the present disclosure is directed to stretching a high loft substrate to facilitate bonding of the substrate with a folded section of that substrate, with one or more other substrates, during converting processes or a combination of these. Through the above processes, a lower loft substrate results, which is more suitable for bonding.

Figure 1:
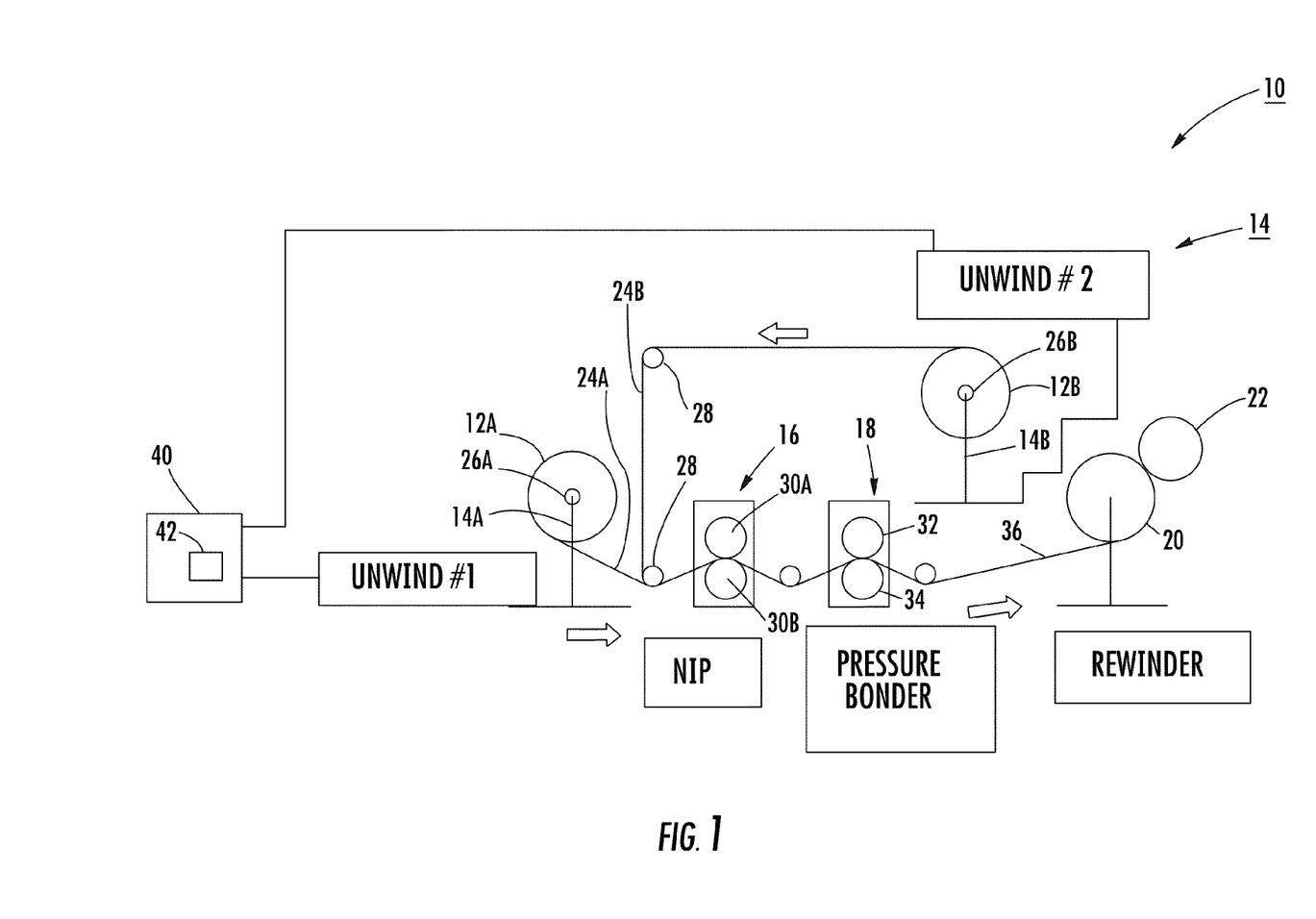
FIG. 1 is a schematic elevational view of one embodiment of a system and process for producing bonded substrates in accordance with an aspect of the present invention.
Figures 2, 2A:
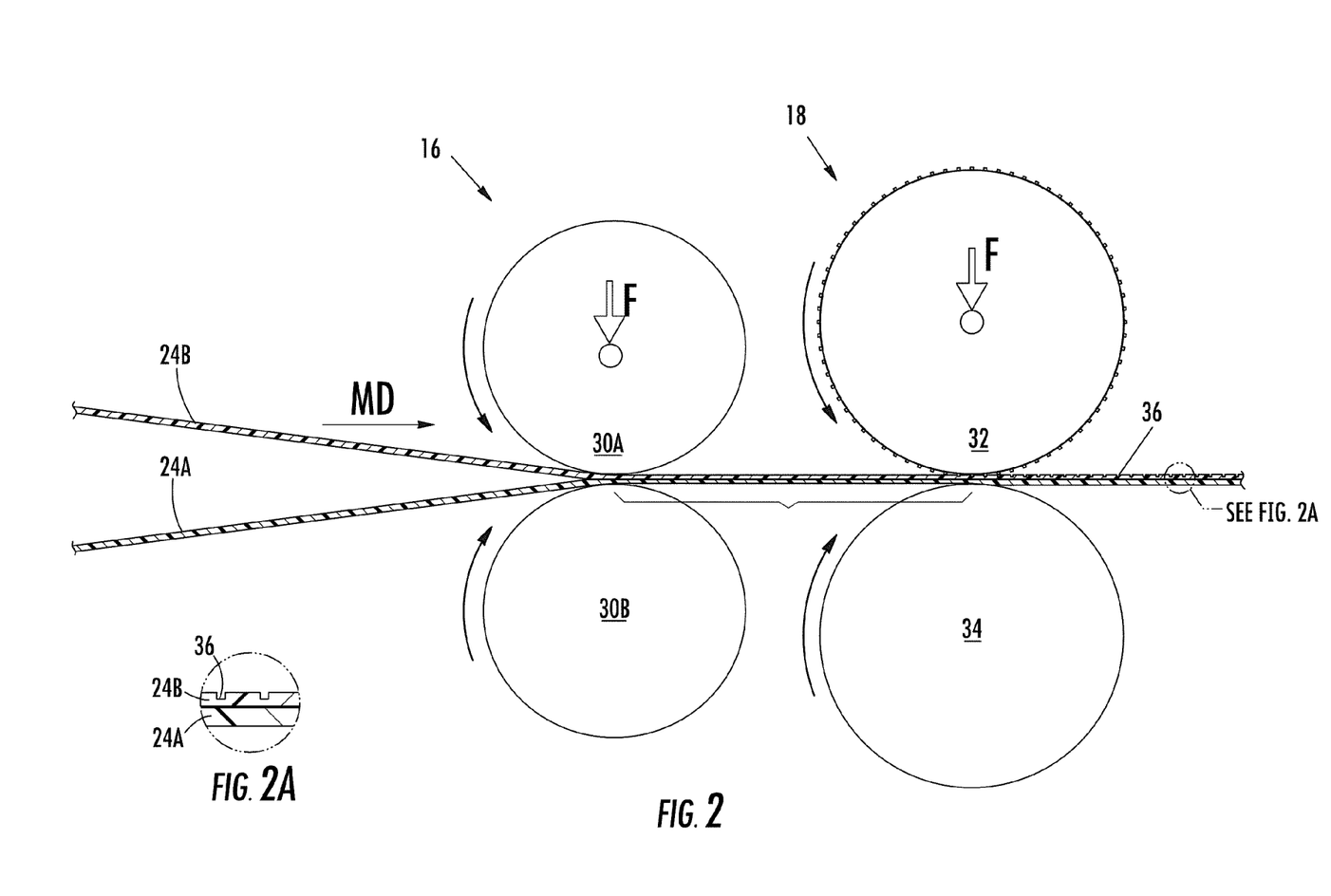
FIG. 2 is a detailed elevational view of a section of the system as in FIG. 1.
Figure 3:
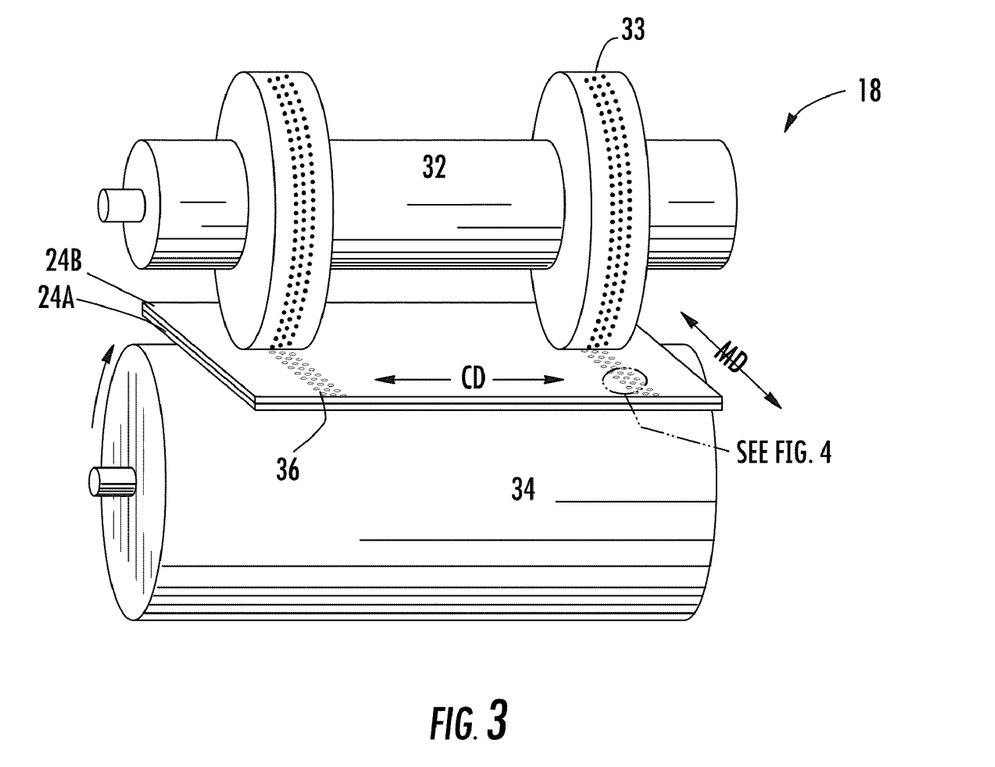
FIG. 3 is a perspective view of a section of the system as in FIG. 1 particularly showing stretched webs of material being bonded according to one aspect of the invention.

Referring now to FIGS. 1-3, an exemplary system and process for producing bonded substrates in accordance with certain aspects of the present invention are illustrated. As shown most clearly in FIG. 1, a process system is designated in general by the element number 10 and broadly includes a plurality of rolls of elastomeric material 12A, 12B, which are unwound by respective unwinds 14A, 14B in an unwind system 14. Respective webs of material 24A, 24B from the rolls of elastomeric material 12A, 12B are nipped together by a nip 16. In this example, the nip 16 operates at a generally slower speed than a pressure bonder system including a pressure bonder 18 located downstream from the nip 16. A speed differential is created by this arrangement, which imparts a stretched state to the webs of material 24A, 24B prior to bonding as will be described in greater detail below. The skilled artisan will instantly appreciate that although multiple rolls of material 12A, 12B are shown by way of example in FIG. 1, a single web of material from a single roll of material can be stretched, converted and bonded according to the invention. Likewise, more than two rolls of material can be stretched for conversion and bonding processes. For instance, the present invention can be used to bond one or more webs of material in various converting processes as described, for example, in U.S. Pat. No. 6,740,200 to Seymour et al., which is incorporated herein by reference thereto. Accordingly, it should be understood that the invention is not limited to the exemplary process system 10 shown in the accompanying figures. It will be further appreciated that although the nip 16 is shown in a vertical roll-roll arrangement, the nip 16 can be an S-wrap arrangement or other suitable arrangement as known in the art.

As shown in FIGS. 1-3, the webs of material 24A, 248 are high loft substrates according to an aspect of the invention that are bonded efficiently when the webs of material 24A, 24B are in a stretched state prior to being bonded by the pressure bonder 18. The stretched state is readily achieved by feeding in less of the webs of material 24A, 24B to the process (e.g., into the nip 16) than what is being taken up by the pressure bonder 18. The result is a lower loft substrate that is more suitable for bonding and producing, for instance, an elastomeric composite 36 as shown or for bonding the webs of material 24A, 24B during converting processes, which is further described below.

As shown more particularly in FIG. 1, the unwind system 14 and its unwinds 14A, 14B are used to unwind the rolls of elastomeric material 12A, 12B as briefly introduced above. In this example, the rolls of elastomeric material 12A, 12B are disposed in the respective unwinds 14A, 14B on respective spindles 26A, 26B. As shown, the webs of material 24A, 24B are fed together by a plurality of a carrier rollers 28 into the nip 16. The nip 16 in this example is a roll 30A and an opposing roll 30B that are spaced apart at a desired, adjustable distance to create a predetermined nip pressure for nipping the webs of material 24A, 24B together prior to entry into the pressure bonder 18. The rolls 30A, 30B apply pressure to the webs of elastomeric material 24A, 24B at a fairly high surface pressure, which can be between about 20 and 300 pounds per linear inch ("PLI"). These and other pressures are described in greater detail below.

More particularly, the nip 16 in FIG. 1 performs the primary stretching of the webs of material 24A, 24B. The speed ratio of the nip 16 relative to the pressure bonder 18 in this example can be varied and in most cases is between about 2:1 and 8:1 and in some cases approximately 4:1 to 6:1. By way of example and not of limitation, the nip 16 and its rolls 30A, 30B can operate from about 600 feet per minute ("FPM") to about 1200 FPM. Accordingly, the pressure bonder 18 in this example can operate from about 1200 FPM to about 2400 FPM. It will be appreciated that the speed of the nip 16 can be slower or much faster than the foregoing examples, and the speed can increased downstream at the pressure bonder 18 or elsewhere in the process system 10 in order to impart stretch or elongation to the webs of material 24A, 24B prior to bonding. The skilled artisan will further appreciate that although the nip/S-wrap 16 is shown upstream of the bonder 18 in this example, a similar nip/S-wrap device can be located downstream to control the web to achieve the desired amount of material stretch. In other words, the pressure bonder system, including a plurality of nips, create the stretch, but the pressure bonder 18 itself does not pull the web through the process. Thus, the arrangement shown in FIG. 1 and the exemplary speeds above are provided merely for illustrative purposes and do not limit the invention to these examples.

With more particular reference to the pressure bonder 18 shown in FIGS. 1-3, the pressure bonder 18 can be a calendaring station such as a calendaring pattern roll 32 and a corresponding or opposing anvil roll 34 (also referred to herein as a bottom or backing roll or roller). As schematically shown, the anvil roll 34 can be fixed onto a base frame and the top roller or pattern roll 32 can be configured to ride on the anvil roll 34. As representatively shown in FIG. 2, a forcing mechanism can be a pneumatic air pressure cylinder configured at the ends of a shaft of the pattern roll 32 to symmetrically exert a desired force F (also referred to herein as a total force, a lineal-pressure value or a loading force) for urging the pattern roll 32 toward the anvil roll 34. Alternatively, the spatial positions of the pattern roll 32 and the anvil roll 34 can be exchanged or otherwise re-arranged, and the anvil roll 34 can be fixed to the base and positioned above the pattern roll 32. Still further, the pattern roll 32 can be offset along a machine direction MD toward either side of the anvil roll 34. The air pressure cylinders can then be installed to operatively exert a loading force F that pushes or otherwise urges the pattern roll 32 upwards and/or sideways against the anvil roll 34.

In the nip region between the pattern roll 32 and the anvil roll 34, the invention can be configured to provide a distinctive lineal-pressure value F, which has the units of force per lineal distance, and may also be referred to as the nip force value. The lineal-pressure value can be determined by the formula:

$$F = Q_T/L;$$

where: $Q_T$=the total force which is exerted by the forcing mechanism to urge the pattern roll 32 toward contact with the anvil roll 34;

L=an average length of contact between the peripheral bonding surfaces of the bonding elements and the surface of the anvil roll 34 if the pattern roll 32 contacted the anvil roll 34 as measured along an axial cross direction of the anvil roll 34.

The average length of contact, L, can be determined by the following formula:

$$L = n*G/S$$

where: n=the number of pin lines; G=bonding surface area of an individual bonding element (e.g., bonding surface area of an individual bonding pin); S=the MD pin spacing distance.

For circular pins; $G=(\pi*d^2)\div 4$. Accordingly, for the circular pins:

$$L = (n*\pi*d^2)/(4*S)$$

where: d=the pin diameter and $\pi$=3.14.

In particular aspects, the lineal pressure value can be at least a minimum of about $0.05*10^6$ N/m. The lineal pressure value can alternatively be at least about $0.05*10^6$ N/m and can optionally be at least about $1*10^6$ N/m to provide desired benefits. In other aspects, the lineal pressure value can be up to a maximum of about $10*10^6$ N/m or more. The lineal pressure value can alternatively be up to about $6\times 10^{6N/M}$ and can optionally be up to about $4.5*10^6$ N/m to provide desired effectiveness. Further details of pressure bonding methods as described by example above can be found in U.S. patent application Ser. No. 11/138,099, which is incorporated herein by reference.

With further reference now to FIG. 3, the pattern roll 32 and the anvil roll 34 are pressed together in an exemplary fashion to bond one or more of the webs of material 24A, 24B as described above. In this example, the pattern roll 32 includes a plurality of bonding protrusions or pins 33 to impart a pattern in the machine direction MD onto the bonded elastomeric composite 36. The skilled artisan will instantly appreciate that the pattern roll 32 and the anvil roll 34 can be arranged other than in the machine direction MD to impart bonding patterns to the elastomeric composite 36. Additionally, other sets of pattern rolls and anvil rolls can be provided having different machine direction and cross machine direction orientations as well as different pins other than the protrusions 33 as shown. Moreover, according to an aspect of the invention, pins are not required to bond the webs of material 24A, 24B since the invention may simply rely on the web materials 24A, 24B deforming plastically under the nip force of the rolls 32, 34. Bonding will therefore occur due to plastic deformation induced internal heating and fusion or melting of the materials 24A, 24B. As known, larger deformation rates imply faster internal heating and increasing bonding speed increases the deformation rate. Also, the smaller a roll diameter the larger the deformation rate. Further, it is known that heat conduction diminishes the effectiveness of a bonding process; therefore, the rolls 32, 34 and any pins 33 are selected from materials, which will not conduct heat efficiently from the webs 24A, 24B.

Figure 4:
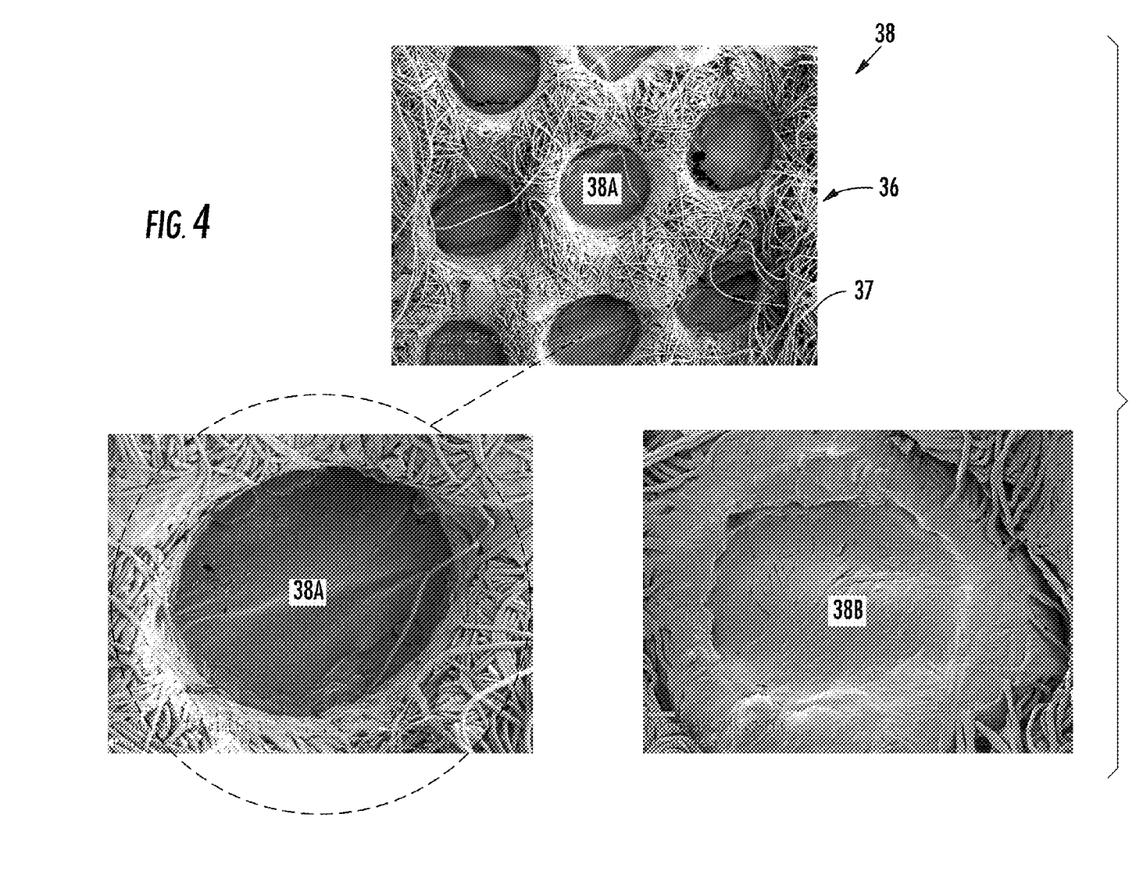
FIG. 4 is a magnified view of surfaces of the stretched webs as in FIG. 3.

Turning now to FIG. 4, a section of the elastomeric composite 36 is shown, which includes a plurality of fibers 37. As shown, a first bond side or pattern roll side 38A of the bonds 38 includes at least some of the fibers 37 that have been melt bonded together. An opposing or bond anvil side 38B of the first bond side 38A is also shown, which most clearly shows compression of the fibers 37 by the bonding force F described above.

The fibers 37 shown in FIG. 4 are an array of filaments that may number from about 200 separate strands to as much as 2600 separate strands. A greater or lesser number of strands, however, are also possible. Additionally, various types of compositions and various processing conditions may be used to form the elastic continuous filaments that form the fibers 37. For example, a Kraton® brand elastic polymer may be fed into an extruder where the polymer is melted at a controlled temperature of between about 260° F. and 460° F., and in certain instances at about 385'F. In other embodiments, depending on the particular polymer employed, the melt temperature may be approximately 470° F. to 480° F. The polymer is then extruded through a predetermined number of apertures in a die head in a generally downward direction into separate continuous filaments at a pressure of approximately 300 to 4000 psi (typically from about 1500 to about 2000 psi). One particular class of polymers that may be used in the present process is the Kraton® G series of polymers distributed by Shell Chemical Company (now available from Kraton Products US-LLC). Various Kraton® polymers may be utilized. However, the skilled artisan will recognize that the invention is not limited to this or any particular polymer or material from which to form the continuous filaments. For example, various materials, including the following, may be used: polypropylene, polyethylene, polyesters, polyethylene terephthalate, polybutane, polymethyldentene, ethylene propylene co-polymers, polamides, tetrablock polymers, styrenic block copolymers, polyhexamethylene adipamide, poly-(oc-caproamide), polyhexamethylenesebacamide, polyvinyls, polystyrene, polyurethanes, thermoplastic polymers, polytrifluorochloroethylene, ethylene vinyl acetate polymers, polyetheresters, polyurethane, polyurethane elastomerics, polyamide elastomerics, polyamides, viscoelastic hot melt pressure sensitive adhesives, cotton, rayon, hemp and nylon.

Other exemplary elastomeric materials that may be used include polyurethane elastomeric materials such as those available under the trademark ESTANE from B.F. Goodrich & Co., polyamide elastomeric materials such as those available under the trademark PEBAX from the Rilsan Company, and polyester elastomeric materials such as those available under trade designation HYTREL from E.I. DuPont De Nemours & Company. However, the invention is not limited to only such elastomeric materials. For example, various latent elastic materials such as the Arnitel-brand polymers may be utilized to provide the necessary elasticity characteristics to the continuous filaments.

Likewise, the above-referenced materials, and others, may be utilized in forming the outer facings of the presently described laminate. In particular, various webs may be utilized that are formed from elastomeric or nonelastomeric fibers. Various polyester elastic materials are, for example, disclosed in U.S. Pat. No. 4,741,949 to Morman et al., which is incorporated herein in its entirety by reference thereto. Other useful elastomeric polymers also include, for example, elastic copolymers of ethylene and at least one vinyl monomer such as, for example, vinyl acetates, unsaturated aliphatic monocarboxylic acids, and esters of such monocarboxylic acids. The elastic copolymers and formation of elastomeric fibers from these elastic copolymers are disclosed in, for example, U.S. Pat. No. 4,803,117, which is also incorporated herein in its entirety by reference thereto.

With brief reference once more to FIG. 1, a controller, computer or programmable logic controller 40 is connected to various components of the process system 10 to control the components. For example, the controller 40 can be electronically connected to the unwinds 14A, 14B, the nip 16, the pressure bonder 18, the rewinder 20 and combinations of these and other components of the process system 10 to control the unwind and rewind speeds as well as the nip pressures described above. More specifically, the controller 40 can be programmed with a software program 42 for setting and controlling desired speeds and pressures and to adjust the speeds and pressures of the components to accommodate different types of substrates being processed by the process system 10.

The present invention may be better understood with respect to the following tests and examples.

TESTING PROCEDURES

The following tests were performed on the samples that were produced. See, e.g., the elastomeric composite 36 and the bonds 38 described above.

Porosity was measured using STM (scientific, technical and medical) procedure number 3801. Porosity was measured using a Frazier air permeability tester. The units are cubic feet per minute per square foot (cfm per $ft^2$) units.

Elongation was measured using test procedure number STM 529-W. Elongation may be tested using any suitable tensile testing equipment, such as those available from the Syntech Corporation of Cary, N.C., or from the Instron Corporation of Canton, Mass.

In a Peel Test, a laminate is tested for the amount of force needed to pull the layers of the laminate apart. The peel strength was measured using testing procedure number STM 751-W. The samples were tested in the cross machine direction. Any suitable tensile testing equipment may be used in order to perform the procedure.

EXAMPLE

The following example was performed in order to determine the effect of stretching webs of material, such as webs 24A, 24B discussed herein, prior to bonding using a bonder such as the bonder 18 as shown in FIG. 1. At least one of the webs of material 24A, 24B was unwound into the nip 16, specifically between the rolls 30A, 30B and stretched prior to the pressure bonder 18 and the rewinder 20. The pressure bonder 18 and the rewinder 20 were processing at a line speed approximately twice that of the unwind system 14 and the nip 16. Stated another way, the pressure bonder 18 and the rewinder 20 took away the material 24A, 24B at a speed twice that of the nip 16 prior to the pressure bonder 18, which ensured that the material 24A, 24B was in a stretched state at the bonder 18. Thirty samples were produced and tested. As shown in the following charts, various product speeds per minute—assuming a product pitch of 29 inches based on the trial pressure bonder—were employed for this test in combination with various pressures of the pattern roll 32 and the anvil roll 34.

| Speed | | Cylinder Pressure | | | | | | | | | |
|---|---|---|---|---|---|---|---|---|---|---|---|
| | | P1 | P2 | P3 | P4 | P5 | P6 | P7 | P8 | P9 | P10 |
| ppm | fpm | (psig) | (psig) | (psig) | (psig) | (psig) | (psig) | (psig) | (psig) | (psig) | (psig) |
| 250 | 604 | 10 | 15 | 20 | 25 | 30 | 35 | 40 | 45 | 50 | 55 |
| 350 | 846 | 10 | 15 | 20 | 25 | 30 | 35 | 40 | 45 | 50 | 55 |
| 450 | 1088 | 10 | 15 | 20 | 25 | 30 | 35 | 40 | 45 | 50 | 55 |

Manual checks of bond strength of the bonded materials 24A, 24B revealed material failure generally before bond failure.

These and other modifications and variations to the present invention may be practiced by those of ordinary skill in the art, without departing from the scope and spirit of the present invention, which is more particularly set forth in the appended claims. In addition, it should be understood that aspects of the various embodiments might be interchanged either in whole or in part. Furthermore, those of ordinary skill in the art will appreciate that the foregoing description is by way of example only and is not intended to limit the invention so further described in such appended claims.

That which is claimed is:

1. A method of bonding material in a bonder system for producing a bonded product, the method comprising the steps of:
    providing at least one quantity of material to a bonder system;
    progressing the at least one quantity of material along the bonder system toward a bonder;
    wherein the at least one quantity of material is introduced into the bonder system at a first speed and attains a second, faster speed as it progresses along the bonder system;
    wherein the difference between the first and second speeds creates a speed differential which imparts a stretched state to the at least one quantity of material;
    using the bonder to bond the at least one quantity of material in the stretched state to at least a second quantity of material also in a stretched state wherein the speed differential has imparted a substantially equal stretched state to the first and second quantities of material simultaneously and prior to the first and second quantity of material entering the bonder; and
    wherein the bonder does not pull the materials.

2. The method of bonding material as in claim 1, wherein the first quantity of material and the second quantity of material are formed from the first quantity of material.

3. The method of bonding material as in claim 1, wherein the quantity of material includes an elastomeric material.

4. The method of bonding material as in claim 3, wherein the quantity of material includes a high loft elastomeric material.

5. The method of bonding material as in claim 1, wherein the quantity of material is an elastomeric material selected from the group comprising a stretch bonded laminate, a vertical filament stretch bonded laminate, a continuous filament stretch bonded laminate and combinations thereof.

6. The method of bonding material as in claim 1, wherein the quantity of material is selected from the group consisting of polyesters, polyolefins, and combinations thereof.

7. The method of bonding material as in claim 1, wherein at least one unwinder is configured to provide at least one roll of elastomeric material to the bonder system.

8. The method of bonding material as in claim 1, wherein the second speed is at least twice as fast as the first speed.

9. The method of bonding material as in claim 1, wherein the bonder is a pressure bonder.

10. The method of bonding material as in claim 1, wherein the bonder is a thermal bonder.

11. The method of bonding material as in claim 1, wherein the quantity of material is stretched from about 25% to about 200% before bonding by the bonder.

12. The method of bonding material as in claim 1, wherein the quantity of material is stretched from about 50% to about 150% before bonding by the bonder.

13. The method of bonding material as in claim 1, wherein the quantity of material is stretched in a machine direction or transverse to the machine direction before bonding by the bonder.

14. The method of bonding material as in claim 1, wherein the quantity of material is stretched transverse to the machine direction and in the machine direction before bonding by the bonder.

15. The method of bonding material as in claim 1, wherein the bonding step imparts a bond to the quantity of material having a bond strength greater than a material strength of the quantity of material such that material failure of the quantity of material occurs before failure of the bond.

16. The method of bonding material as in claim 1, further comprising the step of nipping the quantity of material with a nip to stretch the quantity of material before bonding by the bonder.

17. A method of bonding material in a process system for producing a bonded product, the method comprising the steps of:
    providing a first material and a second material into a bonder system;
    wherein the first and second materials have a first speed upon entering the bonder system and a second, faster speed after progressing along the bonder system, the difference in speed generating a speed differential, wherein the speed differential imparts a stretched state to the first and second material;

introducing the first material and the second material into a nip disposed upstream of a bonder;

passing the first and second material through the nip wherein the nip imparts a substantially equal stretched state simultaneously to the at least first and second quantities of material; and bonding the stretched first and second material together with a bonder of the bonder system wherein the bonder does not pull the material.

18. The method of bonding material as in claim 17, wherein the first and second materials are selected from the group consisting of a elastomeric material, a stretch bonded laminate, a vertical filament stretch bonded laminate, a continuous filament stretch bonded laminate, a polyester, a polyolefin and combinations thereof.

19. The method of bonding material as in claim 18, wherein the quantity of material includes a high loft elastomeric material.

20. The method of bonding material as in claim 17, wherein the second speed is at least twice as fast as the first speed.

21. The method of bonding material as in claim 17, wherein the quantities of material are stretched from about 25% to about 200% before bonding by the bonder.

22. The method of bonding material as in claim 17, wherein the bonding step imparts a bond to the quantities of material having a bond strength greater than a material strength of the quantities of material such that material failure of the quantities of material occurs before failure of the bond.

23. A method of bonding material in a process system for producing a bonded product, the method comprising the steps of:

providing a first material and a second material to a bonder system;

progressing the first and second material toward a pressure bonder;

introducing the first material and the second material into a nip disposed upstream of the pressure bonder, wherein the first and second materials have a first speed upon entering the nip and a second, faster speed after exiting the nip, the difference in speed generating a speed differential, wherein the speed differential imparts a stretched state to the first and second material;

passing the first and second material through the nip wherein the nip imparts a substantially equal stretched state simultaneously to the at least first and second quantities of material; and bonding the stretched first and second material together with the pressure bonder wherein the bonder does not pull the material.

\* \* \* \* \*